United States Patent [19]

Mahler et al.

[11] Patent Number: 4,920,955

[45] Date of Patent: May 1, 1990

[54] SHOCK WAVE SOURCE

[75] Inventors: Mathias Mahler, Erlangen; Manfred Rattner, Buckenhof, both of Fed. Rep. of Germany

[73] Assignee: Siemens Aktiengesellschaft, Berlin and Munich, Fed. Rep. of Germany

[21] Appl. No.: 274,509

[22] Filed: Nov. 22, 1988

Related U.S. Application Data

[63] Continuation of Ser. No. 98,842, Sep. 21, 1987, abandoned.

[30] Foreign Application Priority Data

Oct. 6, 1986 [DE] Fed. Rep. of Germany ....... 3634007

[51] Int. Cl.$^5$ .............................................. A61B 17/22

[52] U.S. Cl. .................................. 128/24 A; 367/175

[58] Field of Search ...................... 128/24 A, 328, 804; 181/142, 402; 367/141, 142, 150, 175

[56] References Cited

U.S. PATENT DOCUMENTS 4,669,472 6/1987 Eisenmenger ...................... 128/328

4,674,505 6/1987 Pauli et al. ......................... 128/328

FOREIGN PATENT DOCUMENTS 3312014 10/1984 Fed. Rep. of Germany ...... 128/328

3502751 7/1986 Fed. Rep. of Germany ...... 128/328

3505894 8/1986 Fed. Rep. of Germany ...... 128/328

3506583 8/1986 Fed. Rep. of Germany ...... 128/328

*Primary Examiner*—Ruth S. Smith

*Attorney, Agent, or Firm*—Hill, Van Santen, Steadman & Simpson

[57] ABSTRACT

A shock wave source of the type suitable for disintegrating calculi in the body of a patient has a shock wave tube which is filled with a shock wave conducting medium, such as a liquid, which is closed at one end by a flexible cover which can be pressed against the patient by the pressure of the medium, and closed at the other end by a membrane of electrically conducting material. A flat coil is provided which is connected to a high voltage pulse generator. An insulting layer is disposed between the membrane and the coil such that the membrane is insulated from the coil at both ends of the coil.

3 Claims, 1 Drawing Sheet

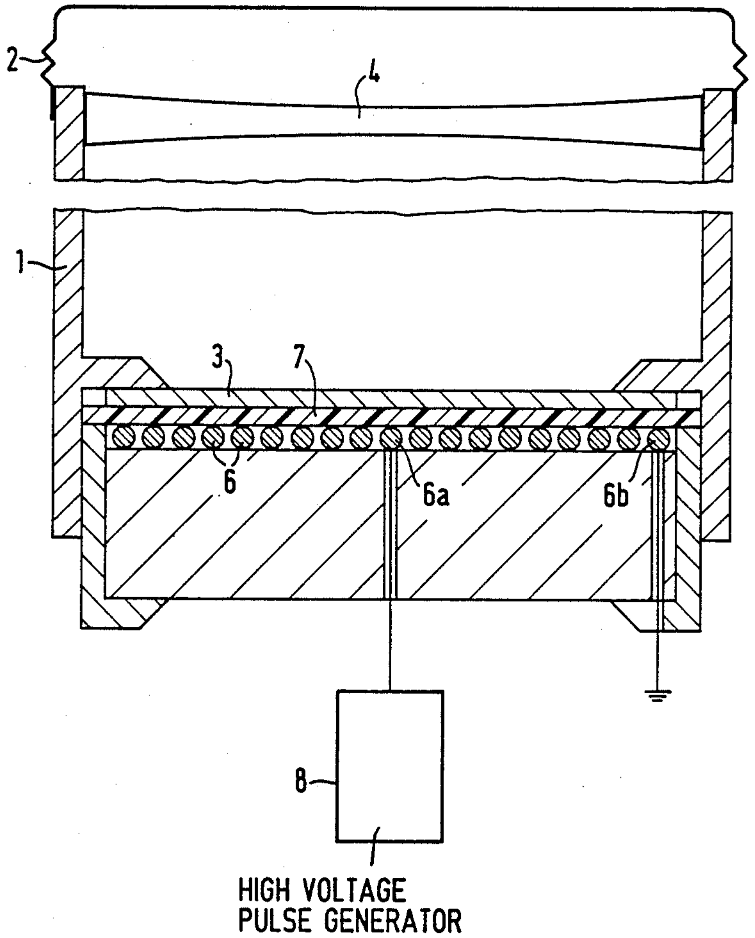
2
4
1
3
7
6
6a
6b
8
HIGH VOLTAGE
PULSE GENERATOR

SHOCK WAVE SOURCE

This is a continuation, of application Ser. No. 098,842, filed Sept. 21, 1987 ABd.

BACKGROUND OF THE INVENTION

1. Field of the Invention

The present invention is directed to a shock wave source of the type suitable for treatment of calculi in the body of a patient, and in particular to such a shock wave source having a tube closed at one end by a flexible cover which can be pressed against the patient and closed at the other end by an electrically conductive membrane which is repelled by a flat coil supplied with high voltage pulses.

2. Description of the Prior Art

Shock wave sources are known which generate focused shock waves which can be directed at a calculus to be disintegrated in the body of a patient, for example a kidney stone. The calculus is shattered to such a degree that it can be eliminated naturally. The generation of the shock wave is undertaken by discharging a high voltage capacitor through a flat coil which may, for example, be in the form of a helical winding. An electrically conductive membrane is disposed adjacent to, but spaced from, the coil, and is repelled upon the occurrence of the high voltage pulse in the coil. The sudden movement of the membrane generates a shock wave in the volume between the membrane and the flexible covering. This shock wave is directed through a shock wave conducting medium in volume at the calculus by means of an acoustic lens in the shock wave tube.

Shock wave sources of this type are known wherein both one end of the coil and the membrane lie at ground potential. If a high voltage of, for example 20 kV is applied to the flat coil for generating a shock wave, the full high-voltage will be between a point of the flat coil and the membrane. The layer of insulation between the flat coil and the membrane must therefore have dimensions capable of insulating the entire high-voltage. Nonetheless, arcing is not always successfully avoided. A destruction of the membrane occurs as a result of such arcing.

SUMMARY OF THE INVENTION

It is an object of the present invention to provide a shock wave source of the type described above wherein the risk of voltage arcing between the flat coil and membrane is reduced in comparison to conventional devices.

The above object is achieved in accordance with the principles of the present invention in a shock wave source wherein the membrane is electrically insulated from both ends of the flat coil. In contrast to conventional shock wave sources, therefore, the membrane and one coil end are not grounded, so that the entire high-voltage is present between the membrane and the coil. As a result of the electrical insulation of the membrane from both coil ends, the insulating distance for the entire high-voltage is equal to twice the distance between the coil and the membrane, so that the risk of arcing is extremely slight.

DESCRIPTION OF THE DRAWING

The single FIGURE is a side sectional view, with a schematically indicated voltage source, of a shock wave tube constructed in accordance with the principles of the present invention showing the primary elements thereof.

DESCRIPTION OF THE PREFERRED EMBODIMENTS

A shock wave tube 1 has a side thereof, which is to be applied to a patient, closed by an elastic cover 2. An opposite end of the shock wave tube is closed by a membrane 3 consisting of electrically conductive material. The volume surrounded by the shock wave tube 1, the cover 2, and the membrane 3 is filled with a shock-wave conducting coupling agent, such as water. An acoustic lens 4 for focusing the generated shock waves is disposed in this volume. Generation of the shock waves is achieved with a flat coil disposed opposite the membrane, which may be helically wound, and which is separated from the membrane 3 by a layer 7 of insulating material. One terminal of the flat coil is grounded, and the second terminal is connected to a high-voltage pulse generator 8.

Upon actuation of the high voltage pulse generator 8, the flat coil is briefly and rapidly energized, and the membrane 3 is rapidly repelled therefrom due to the eddy currents generated in the membrane 3 consisting of electrically conductive material. A shock wave thus propagates through the coupling agent in the shock wave tube 1 and is focused by the acoustic lens 4 at a calculus disposed in a patient.

The membrane 3 is electrically insulated from both ends *6a* and *6b* of the flat coil 6. The total insulating distance, which the maximum high voltage must withstand, is thus equal to twice the thickness of the layer 7 of insulating material. The risk of arcing between any location of the flat coil 6 and the membrane 3 is consequently extremely low. If an arcing were to occur, it would usually proceed between the coil end *6a*, the membrane 3 and the coil end *6b*. Thus the entire insulating distance is equal to the aforementioned, twice the distance between the flat coil 6 and the membrane 3, so that an adequate insulation is guaranteed, even if the layer 7 of insulating material is quite thin.

Although modifications and changes may be suggested by those skilled in the art, it is the intention of the inventors to embody within the patent worded hereon all changes and modifications as reasonably and properly come within the scope of their contribution to the art.

We claim as our invention:

1. A shock wave source comprising:

a housing enclosing a volume filled with a shock wave conducting medium;

an elastic cover closing one end of said volume;

a membrane consisting of electrically conductive material insulated from ground and closing an opposite end of said volume;

a coil disposed substantially parallel to and spaced from said membrane, said coil having opposite ends, one of said opposite ends being connected to ground and the other of said opposite ends being connected to a high voltage pulse generator such that energization of said coil by said pulse generator rapidly repells said membrane therefrom and generates a shock wave in said medium; and an electrically insulating layer disposed between said coil and said membrane such that both of said opposite ends of said coil are electrically insulated from said membrane.

2. A shock wave generator is claimed in claim 1 wherein said coil is a flat coil.

3. A shock wave generator comprising:

a housing containing a volume filled with a shock wave conducting medium;

an electrically conductive membrane disposed in contact with said medium;

means for generating a field for rapidly moving said membrane to generate a shock wave in said medium, said means for generating a field including a connection to a high voltage supply and a connection to ground; and means for completely electrically insulating said membrane from ground and said means for generating a field.

* * * * *